United States Patent [19]

Prevedello et al.

[11] 4,279,834

[45] Jul. 21, 1981

[54] METHOD FOR SYNTHESIZING DINITRILES, PRODUCTS OBTAINED THEREBY AND THEIR DERIVATIVES

[75] Inventors: Aldo Prevedello, San Donato Milanese; Maurizio Brunelli, Milan; Edoardo Platone, Asti, all of Italy

[73] Assignee: Anic S.p.A., Palermo, Italy

[21] Appl. No.: 113,093

[22] Filed: Jan. 17, 1980

Related U.S. Application Data

[63] Continuation of Ser. No. 899,797, Apr. 25, 1978, abandoned.

[30] Foreign Application Priority Data

Apr. 26, 1977 [IT] Italy .................................. 22806 A/77
Feb. 24, 1978 [IT] Italy .................................. 20560 A/78

[51] Int. Cl.$^3$ .................. C07C 120/00; C07C 121/46; C07C 121/20; C07C 121/26
[52] U.S. Cl. ........................... 260/464; 252/401; 528/341; 528/344; 528/346; 528/347; 260/453 AL; 260/465 H; 260/465.8 R; 564/367; 564/372; 564/448; 564/457; 564/461; 564/491; 564/493; 564/511
[58] Field of Search ............. 260/465.8 R, 464, 465 H

[56] References Cited

U.S. PATENT DOCUMENTS 3,936,490  2/1976  Hoffmann et al. ............ 260/465.8 R

FOREIGN PATENT DOCUMENTS 1590082  4/1970  France .

OTHER PUBLICATIONS

C.A., V49, (1955), 13070f, Gingras et al.
C.A., V80, (1974), 95438n, Popandova et al.
C.A., V66–75, coll. (8th) index, 1971, p. 13951s.
C.A., V57, (1962), 7117f, Tsukamoto et al.

*Primary Examiner*—Joseph Paul Brust
*Attorney, Agent, or Firm*—Morgan, Finnegan, Pine, Foley & Lee

[57] ABSTRACT

New dinitriles are prepared by reacting an alpha, beta saturated nitrile with an alpha, beta unsaturated nitrile. For this preparation subzero temperatures are preferred. Higher diamines can be prepared by hydrogenating the dinitriles thus obtained, such diamines being reacted with a dicarboxylic acid or a salt, ester or chloride of such an acid to prepare polyamides having an amorphous character, i.e. transparent polyamides.

7 Claims, No Drawings

METHOD FOR SYNTHESIZING DINITRILES, PRODUCTS OBTAINED THEREBY AND THEIR DERIVATIVES

This is a Rule 60 Continuation Application of Ser. No. 899,797 filed on Apr. 25, 1978 now abandoned and which claims the priority of Italian patent application No. 22806 A/77 filed on Apr. 26, 1977 and Italian patent application No. 20560 A/78 filed on Feb. 24, 1978.

This invention relates to a method for the synthesis of dinitriles, to the products thus obtained and to their derivatives.

There are known in the literature several methods for the synthesis of the dinitriles, for example of dicarboxylic acids, through the formation of ammonium salts and subsequent dehydration, from diamides by dehydration, from unsaturated nitriles by hydrocyanation, by reaction between dihalides and cyanides, by reductive dimerization of acrylonitrile and other nitriles which are alpha-, beta-unsaturated, by reaction of nitriles with omega-bromo-nitriles.

It is known, moreover, that it is possible to add, to the alpha-, beta-unsaturated nitriles, the so-called "pseudoacidic" nitriles, such as benzyl cyanide, alpha-phenyl propionitriles, and malononitrile. McRae and Baunard report, furthermore, the synthesis of dinitriles by reacting an alpha-, beta-unsaturated nitrile with potassium cyanide.

An object of the present invention is to provide a method for the synthesis of dinitriles, which makes it possible to obtain variously substituted dinitriles with good yields and selectivity.

The method of this invention comprises the step of reacting an alpha-beta-saturated nitrile having the general structural formula

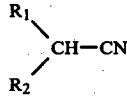

wherein $R_1$ and $R_2$, equal or different from one another, can be hydrogen, an aliphatic hydrocarbon, cycloaliphatic hydrocarbon, saturated or unsaturated radical, with an alpha, beta-unsaturated nitrile having the following structural formula:

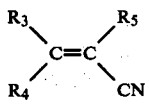

wherein $R_3$ and $R_4$ can be aliphatic hydrocarbon or cycloaliphatic hydrocarbon radicals and $R_5$ is hydrogen, an aliphatic hydrocarbon, cycloaliphatic hydrocarbon, or aromatic radical.

The resultant dinitrile derives from the addition of the alpha, beta-saturated nitrile to the double bond of the alpha-beta unsaturated nitrile and has thus the following structural formula:

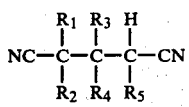

wherein $R_1$ $R_2$ $R_3$ $R_4$ and $R_5$ have the meanings indicated above.

Examples of alpha-beta saturated nitriles are: acetonitrile, propionitrile, butyronitrile, isobutyronitrile, valeronitrile and, in general, the nitriles of saturated, straight-line or branched carboxylic acids, cyclohexanecarbonitrile, cyclopentanecarbonitrile, cyclohexaneacetonitrile, cyclopropanecarbonitrile, 3-cyclopentaneacetonitrile, 3-cyclopentanepropionitrile, 2-methylcyclopentaneacetonitrile, 3-phenylpropionitrile and others.

Examples of alpha, beta unsaturated nitriles are: 3,3-dimethylacrylonitrile, 3,3-diethylacrylonitrile, 2,3,3-trimethylacrylonitrile, 1-cyclohexenecarbonitrile, 1-cyclopentenecarbonitrile, 3-methylcinnamonitrile, 2,3-dimethylcinnamonitrile, 3,7-dimethyl-2,6-octadienenitrile ("geranonitrile"), cyclogeranonitrile and others.

Thus, by variously combining the alpha, beta saturated nitriles with alpha, beta unsaturated nitriles, there are obtained a variety of dinitriles which are useful, above all, after their hydrogenation to diamine, for the synthesis of amorphous polyamides.

A few dinitriles which can be obtained with the method according to the present invention, are:

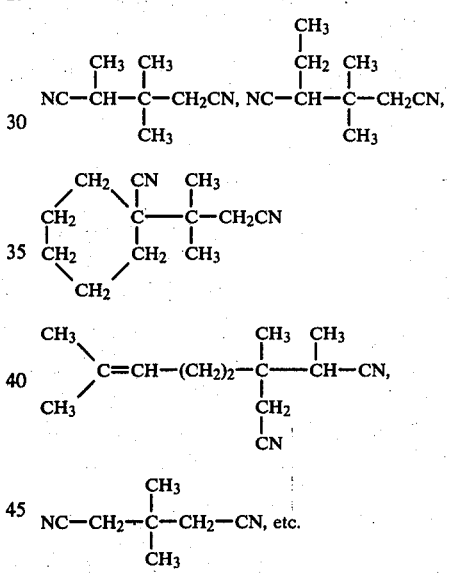

Of these compounds, only the last named one is known from the literature.

The reaction in the light of the present invention consists in contacting the alpha, beta saturated nitrile with a strong base, whereafter there is added, to the mixture thus obtained, the alpha, beta unsaturated nitrile. After a few minutes as from the addition of the alpha, beta unsaturated nitrile, the reaction is stopped with ammonium chloride.

The thusly formed dinitrile is separated according to conventional procedures. For example, after having evaporated off the solvent, water is added and the extraction is effected by means of a water-immiscible solvent. The dinitrile which has been extracted in this way can possibly be purified by distillation under reduced pressures.

As regards the stoichiometry of the reaction, the alpha, beta saturated and unsaturated nitriles can be used in equimolar amounts. The two reactants can be used as such or diluted with an inert solvent such as ethyl ether, tetrahydrofuran or hydrocarbonaceous solvents. The strong bases which can be used are the amides of alkali metals, such as sodamide, potassium amide or lithium amide, the hydrides of alkali metals or of alkaline earth metals, such as sodium hydride, lithium hydride, potassium hydride, calcium hydride and others, the metallic alkyls such as lithium-nor.butyl, lithium-isopropyl and others.

The strong bases listed above must be in an at least stoichiometric amount relative to the alpha, beta saturated and unsaturated nitriles and thus, as a rule, they are within the range of from 1 to 5 mols of base per mole of saturated nitrile, preferably from 1 to 1.8 mols per mol of saturated nitrile. It is possible, obviously, to adopt a ratio below the stoichiometrical one, but, if so, in addition to having a lower yield, there is also a selectivity drop which is caused by the formation of undesirable products.

It is to be noted that the strong bases which are used can either be preformed or formed "in situ" (for example, sodamide can be obtained by charging elemental sodium in ammonia in the presence of appropriate catalysts.

It is advisable to use a solvent which is capable of dissolving, at least in part, the strong base which is adopted. For example, for the amides of alkali metals, it is preferable that ammonia be used, whereas for the lithium alkyls it is preferred that ethyl ether or tetrahydrofuran be used, or hexane. At any rate, it is not appropriate to use, as the solvents, substances which interfere with the basic substances, such as acids, esters and the like.

The reaction takes place quickly, already at temperatures below 0° C., so that there is no need to raise the temperature in order to speed up the reaction progress. The reaction takes place normally between −80° C. and +70° C., the range of from −50° C. to −10° C. being preferred. The reaction progresses through three discrete stages.

In the first stage, the alpha, beta saturated nitrile is contacted with the strong base.

In the second stage, there is added, to the mixture thus obtained, the unsaturated alpha, beta nitrile, thus enabling the anion of the alpha, beta unsaturated nitrile (as formed in the first stage), to be added to the double bond of the alpha, beta unsaturated nitrile.

The third stage consists in stopping the reaction with an acid, or with a salt of a strong acid and a weak base, preferably ammonium chloride, which neutralize the anion and originate the dinitrile.

Just because the reaction can be regarded as a sequence of three orderly subsequent stages, the order for the addition of the nitriles is fixed. The alpha, beta saturated nitrile is introduced in the reactor, whereafter, upon reaction of the nitrile with the base, the alpha, beta unsaturated nitrile is poured into the reaction mixture.

As regards the reaction times, the first stage, or ionization of the alpha, beta saturated nitrile takes from 10 mins. to 100 mins., and more frequently it takes from 20 mins. to 40 mins.

The second stage, or reaction of the anion of the alpha, beta saturated nitrile with the alpha, beta unsaturated nitrile, requires preferably, between the completion of the addition of the alpha, beta unsaturated nitrile and the reaction with ammonium chloride, a time from 1 min. to 60 mins., usually from about 3 mins. to 10 mins.

Ammonium chloride is to be used in a molar ratio equal to or higher than that of the strong base, preferably in a ratio of from about 1 to about 5 per mol of the base. Usually, it is enough to have a ratio of from 1.1 to 2 mols of ammonium chloride per mol of base used.

Ammonium chloride can be poured cautiously into the reaction mixture: as an alternative, it is preferred to siphon the reaction mixture into an externally cooled vessel which contains ammonium chloride: the latter can be solid, dissolved or slurried in an inert solvent, for example dissolved in water or slurried in ethyl ether.

The reaction is insensitive to pressure differentials, so that it can be performed either under an overpressure or under atmospherical pressure.

Another object of the present invention is to provide methods for the preparation of 1,5-pentadiamines having the general formula:

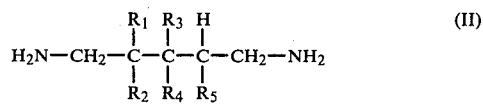

The literature reports many patents and publications which relate to the synthesis of transparent polyamides.

The principal method for preparing such polymer is the polycondensation of a particular class of aliphatic diamines, and is characteristic in that the main chain is substituted by one or more alkyl groups. The polyamides obtained therefrom generally show a very low crystallinity and very often they are wholly amorphous, thus they are transported.

This phenomenon is an outcome of the steric hindrance caused by the presence of the alkyls.

The substituted aliphatic diamines which are best known from the literature are: 2,2,4-trimethyl- and the 2,4,4-trimethyl hexamethylenediamine deriving from isophorone, the 3-aminomethyl-3,5,5-trimethylcyclohexylamine also deriving from isophorone, a mixture of diamines based on trimers of cyclopentadiene and, lastly, the 2,2-dimethyl pentanediamine. These diamines, however, cannot be obtained in a convenient and cheap manner. Their preparation in fact, involves quite a series of reactions which sometimes use toxic reagents such as hydrogen cyanide.

The methods according to the present invention are characterized in that a derivative having the general formula (I) reported hereinabove is reduced, either with the aid of a catalyst, or not.

In the case of the catalytic reduction, there can be used as catalysts several metals, more particularly palladium, platinum, rhodium or ruthenium, which can be used in the pure state or also deposited on an inert supporting member such as activated carbon or alumina, or also in the state of an oxide and otherwise. Other catalysts can be metals of the VIII Group of the Periodic Table, such as nickel, nickel Raney, cobalt, cobalt Raney and others.

The working conditions are selected as a function of the catalyst which is adopted. In the case in which the catalyst is a noble metal, there is used, preferably, as the solvent an aliphatic carboxylic acid such as acetic acid, propionic acid, and like acids, acetic acid being, however, preferred.

There can be used other solvents, such as, in the case of rhodium, an ammoniacal solution.

The temperature at which the reduction is carried out is comprised between 10° C. and 150° C., room temperature being preferred. The reduction, moreover, can be conducted under a wide range of pressures of hydrogen, from values near the atmospherical pressure up to 300 atm. preferably between 30 atm and 150 atm. When the catalyst which is adopted is a metal of the VIII Group of the Periodic Table such as cobalt Raney or nickel Raney, the presence of a solvent is not essential. It is preferred, though, to work with a diluent such as ethanol or dioxan in variable proportions. It is preferred, on the other hand, to work with ammonia being present so as to minimize the formation of secondary and tertiary amines. The quantity of ammonia to be used is preferably between 5 and 20 mols per mol of dinitrile. The reduction can be carried out, preferably, at a temperature comprised between 60° C. and 150° C. and under hydrogen pressures variable from 1 atm. to 700 atm, preferably between 120 atm and 450 atm.

The hydrogenation of the compound (I) can also be carried out without any catalyst, for example with sodium and alcohol, with diborane and otherwise. The pentadiamines having the general formula (I) thus obtained can be used with advantage not only for the synthesis of polyamides, on the properties of which a discussion will be made hereinafter, but also as stabilizers or antioxidants for lubricant oils, as agents for treating polyepoxides, as intermediates for the synthesis of the corresponding isocyanates and other uses.

Yet another object of the present invention is to indicate the synthesis of amorphous polyamides, which are thus transparent, by means of the polycondensation of pentadiamines of the formula (II) with bicarboxylic aliphatic, cycloaliphatic or aromatic acids or derivatives of same, such as esters and halides.

For the synthesis of these novel polyamides, conventional polycondensation methods can be adopted. It is possible, for example, to heat together the diamine and the diacid, as such or in the form of salts, with water or in an anhydrous environment, with no oxygen being present, at temperatures and under pressures which are preferably high, and the completing the polycondensation by heating, for example, in vacuum to dispel the water. As a modification, the salt can be heated in an inert solvent such as m-cresol. In order that the mol wt of the polymers may be limited, a slight excess of the diamine or the diacid can be added, or a reagent capable of forming a monofunctional amide bond, such as acetic acid. The same reaction can likewise be effected between the diamine and a diester of a dicarboxylic acid. Methods of interface polycondensation can also be adopted by reacting a bichloride of a dicarboxylic acid, dissolved in a water-immiscible organic solvent, with an aqueous solution of a diamine which contains another proton acceptor. Various solvents can be used, such as benzene, toluene, chloroform, methylene chloride, carbon tetrachloride and others. As proton acceptors can be used: the diamine itself, a tertiary organic base such as triethylamine, a mineral base such as calcium hydroxide, or the solvent itself if this is an amide, for example dimethylacetamide. As dicarboxylic acids there can be used, for example, glutaric acid, adipic acid, monomethyladipic, dimethyladipic and trimethyladipic acids, pimelic acid, suberic acid, azelaic acid, sebacic acid, undecanoic acid, dodecanedioic acid, tetradecanedioic acid, octadecanedioic acid, 3-ethyl sebacic acid, 3-butylsuberic acid, 1,4-cyclohexanebicarboxylic acid, cyclopentane-1,3-bicarboxylic acid, isophthalic acid, 4-methylisophthalic acid, terephthalic acid, 2-methylterephthalic acid, naphthalenebicarboxylic acids and many others.

As the chlorides of the diacids, there can be used: o.phthaloyl chloride,, the chlorides of methoxy-, dimethoxy-, and ethoxyisophthaloyl, terephthaloyl chloride, 2,5-dibromoterephthaloyl chloride, the acid chlorides of the succinic, adipic, sebacic acids and others.

As esters there can be used ethyl oxalate, butyl oxalate, butyl phenylmalonate, the methyl- and phenyl esters of the ortho-, iso- and terephthalic acids of the pyridine-2,5-dicarboxylic acid of the furan-2,5-bicarboxylic acid, and others.

Another object of the present invention is to suggest a method for the preparation of copolymers obtained by reaction with one or more of the acids or of the derivatives suggested above, with one or more diamines, at least one of the latter diamines being encompassed in the general formulae of the present application.

For example, a dicarboxylic acid, its diester or its dichloride can be reacted with one of the diamines according to the present invention, the latter diamine being admixed with another diamine such as hexamethylenediamine, copolyamides being thus obtained, which exhibit especially interesting properties.

The polyamides prepared according to the method of this invention exhibit a good solubility in m-cresol, dimethylsulphoxide, dimethylformamide. These polyamides are swollen by chloroform and by ethanol and, sometimes, in certain cases of aliphatic polyamides, they are dissolved by these solvents. They, conversely, are unaffected by acetone, ether and petroleum ether. Consistently with the particular dicarboxylic acid which is used, the polyamides according to the present invention display a glass transition (Tg) which lies within a wide temperature range. Of particular interest are the polyterephthalamides, which have a high Tg and thus an improved dimensional stability which enables them to be used even at comparatively high temperatures.

All the polyamides of this invention are amorphous, as shown by the X ray analysis performed on the polymers as such as well as on the annealed polymers. The thermal analysis of these samples, performed on the Differential Scanning Calorimetry (D.S.C.), in addition to indicating the Tg, shows that the polyamides of this invention are thermally stable since they do not display any appreciable signs of decomposition at temperatures up to about 300° C. The polyamides have been characterized, in addition, by measuring their water absorptivity and inherent viscosity (inh. η) at 130° C. in a 0.5% solution in 98%-$H_2SO_4$.

The attitude of these polyamides towards film formation, the good adhesion to glass and to certain metals, their good solubility in a few organic solvents and their transparency (due to their amorphous structure) suggest the exploitation of such polyamides in the industry of lacquers and varnishes and, above all, in the manufacture of moulded transparent articles.

To provide a better understanding of the present invention, a few explanatory examples are given without any limitation of this invention.

EXAMPLE 1

Preparing 2,3,3-trimethyl-pentane dinitrile

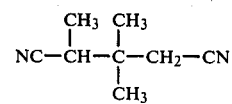

A one-liter flask, equipped with mechanical stirrer having glass vanes, a dropping funnel with a nitrogen intake and an intake for ammonia, is charged under a nitrogen blanket with 300 mls of liquid ammonia which has been carefully dehydrated through a first pass on potassium hydroxide in pellets and then through a second pass on finely crushed elemental sodium.

During the stage of ammonia charging and during the remainder of the reaction, the flask is immersed in a bath of alcohol and dry ice, the temperature of the bath being constantly maintained at $-41°$ C.$--38°$ C.

Meanwhile, in a weighing jar containing anhydrous hexane, there are prepared 5.06 grams (0.22 mol) of elemental sodium in tiny fragments.

The reaction flask is then charged, with stirring and under a slight stream of anhydrous nitrogen, with a pinch of ferric chloride (about 200 milligrams) and then with one tenth of the metallic sodium which had been prepared beforehand.

After 10 mins. the flask is charged with the remaining sodium pieces, an operation which takes 10 mins. approximately.

After 15 additional mins. there are poured in the flask during 5 minutes, 11 grams (0.2 mol) of anhydrous propionitrile diluted with 20 mls of anhydrous ethyl ether.

After a pause of 30 mins. there are added, during 5 mins., 16.2 grams (0.2 mol) of 3,3-dimethyl acrylonitrile of commercial purity (i.e. 95%) diluted with 20 mls. of anhydrous ethyl ether.

5 mins. after the completion of the addition of the 3,3-dimethyl acrylonitrile, the reaction mixture is siphoned into an Erlenmeyer flask containing 22.4 grams (0.4 mol) of ammonium chloride slurried in 150 mls of ethyl ether, the flask having a magnetic stirrer and being cooled externally by an alcohol and dry ice bath.

Ammonia is then evaporated off by immersing the flask in a crystallizer filled with alcohol. During evaporation, there are added about 150 mls of ethyl ether, whereafter, on completion of the evaporation of ammonia, 150 mls of water are added. The two phases are then split. The aqueous phase is extracted six times with ethyl ether (50 mls each time). The ethereal extracts are combined, dried over anhydrous sodium sulphate and then filtered. Ether is then distilled off in a rotary evaporator under a pressure of about 200–250 mls. There are obtained 30 grams of raw product which still contain ethyl ether. The raw product is then distilled in a vacuum in a 30-cm Vigreux column. The principle fraction is composed by 20.2 grams (yield 74.8%) of 2,3,3-trimethyl-pentanedinitrile, having a boiling point of $88°$ C.-$89°$ C. under about 0.3 mmHg.

The most significant spectroscopical characteristics of $$NC-\underset{\underset{CH_3}{|}}{\overset{CH_3}{\overset{|}{CH}}}-\overset{CH_3}{\underset{|}{C}}-CH_2CN$$

are: I.R.: stretching of CN at about 2250 cm$^{-1}$ N.M.R.: Chemical Shifts relative to hexamethyldisilazane-deuterated chloroform (i.e. chloroform which has a hydrogen atom replaced by a deuterium atom) [HMDS-CDCl$_3$] solvent:

$-\underset{|}{CH}- \quad = 2.66$ (q) (J = 7 Hz)

-continued $-CH_2- \quad = 2.39$ (s)

$CH_3-\underset{\underset{CN}{|}}{\overset{H}{\overset{|}{C}}}- \quad = 1.25$ (d) (J = 7 Hz)

$-\underset{\underset{CH_3}{|}}{\overset{CH_3}{\overset{|}{C}}}- \quad = \begin{pmatrix} 1.17 \text{ (s)} \\ 1.14 \text{ (s)} \end{pmatrix}$ M.S.: m/e (relative intensity, %): 82(100), 55(70), 76(54), 41(40), 54(32), 39(28), 27(26), 69(20), 137(M+1)+ (3)

EXAMPLE 2

Synthesizing 3,3-dimethylpentanedinitrile $$NC-CH_2-\underset{\underset{CH_3}{|}}{\overset{CH_3}{\overset{|}{C}}}-CH_2CN$$

The reaction procedure (apparatus, times, temperature, order of introduction of the reactants) are the same as in EXAMPLE 1.

The following quantities are charged:

| | |
|---|---|
| ammonia | : 300 mls |
| ferric chloride | : 0.2 grams approx. |
| Elemental sodium | : 5.06 grams (0.22 mol) |
| acetonitrile | : 8.2 grams (0.2 mol) diluted with 20 mls of anh. ethyl ether |
| 3,3-dimethylacrylonitrile | : 8.2 grams (0.2 mol) diluted with 20 mls of anhydrous ethyl ether. |

The raw product of the reaction is processed as indicated in EXAMPLE 1.

There are obtained 12.2 grams (yield 50%) of 3,3-dimethyl pentanedinitrile which boils at $95°$ C.-$96°$ C. under a pressure of about 1.5 mmHg and solidifies at room temperature.

The principal spectroscopical characteristics of this compound are:
I.R.: stretching of the $-C\equiv N$ at about 2250 cm$^{-1}$
N.M.R.: chemical shifts relative to hexamethyldisilazane-deuterated chloroform (i.e. chloroform which has a hydrogen atom replaced by a deuterium atom) [HMDS-CDCl$_3$] solvent $-CH_2-=2.37$ (s) $-CH_3=1.19$ (s)

M.S. Mass Spectroscopy m/e (relative intensity, %) 82(100), 55(49), 39(26), 41(20), 54(16), 27(14), 53(11), 29(11), 122(M+)(7), 123(M+1)+(5)

EXAMPLE 3

Synthesizing $$\begin{array}{c} CH_2-CH_2 \\ CH_2 \\ CH_2-CH_2 \end{array} \underset{CH_3}{\overset{CN\ CH_3}{\underset{|}{\overset{|}{C}-\overset{|}{C}-CH_2-CN}}}$$

3-(1-cyanocyclohexyl)-3-methyl-butyronitrile

The reaction procedure (apparatus, times, temperature, order of introduction of the reactants are the same as for EXAMPLE 1.

The following amounts are charged:

| | |
|---|---|
| ammonia | : 300 mls |
| ferric chloride | : 0.2 grams approx. |
| elemental sodium | : 5.06 grams (0.22 mol) |
| cyclohexanecarbonitrile | : 21.8 grams (0.2 mol) diluted with 20 mls of anhydrous ethyl ether |
| 3,3-dimethylacrylonitrile | : 16.2 grams (0.2 mol) diluted with 20 mls of anhydrous ethyl ether |
| ammonium chloride | : 22.4 grams (0.4 mol) slurried in 150 mls of ethyl ether |

The raw product of the reaction is processed just as in EXAMPLE 1.

There are obtained 26.6 grams (yield 70%) of 3-(1-cyanocyclohexyl)-3-methyl butyronitrile which boils at 99° C.-100° C. under a pressure of 0.15 mmHg.

The principal spectroscopical characteristics of this compound are:

I.R.: Stretching of the —C≡N at about 2250 cm$^{-1}$

N.M.R.: Chemical shifts relative to HMDS-CDCl$_3$ solvent. —CH$_2$—CN=2.50 (s)

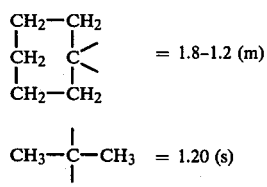 = 1.8-1.2 (m)

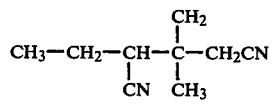 = 1.20 (s)

M.S.: m/e (relative intensity, %) 109(100), 82(33), 67(19), 41(15), 110(9), 108(9), 39(8), 55(8), 191(M+1)(3).

EXAMPLE 4

Synthesizing 2-ethyl-3,3-dimethyl pentane dinitrile $$CH_3-CH_2-\underset{\underset{CN}{|}}{CH}-\underset{\underset{CH_3}{|}}{\overset{\overset{CH_2}{|}}{C}}-CH_2CN$$

The reaction procedure (apparatus, times, temperature, order of introduction of the reactants) are the same as in EXAMPLE 1.

The following amounts are charged:

| | |
|---|---|
| ammonia | : 300 mls |
| ferric chloride | : 0.2 grams approx. |
| elemental sodium | : 5.06 grams (0.22 mol) |
| butyronitrile | : 13.8 grams (0.2 mol) diluted with 20 mls of anhydrous ethyl ether |
| 3,3-dimethylacrylonitrile | : 16.8 grams (0.3 mol) diluted with 20 mls of anhydrous ethyl ether. |
| ammonium chloride | : 16.8 grams (0.3 mol) slurried in 150 mls of ethyl ether. |

The raw product of the reaction is processed as in EXAMPLE 1.

There are obtained 20.1 grams (yield 67%) of 2-ethyl-3,3-dimethyl pentanedinitrile having a boiling point of 87° C.-89° C. under a pressure of 0.7 mmHg.

Its principal spectroscopical characteristics are:
I.R.: stretching of —CN at about 2245 cm$^{-1}$
N.M.R.: chemical shifts relative to hexamethyldisilazane-deuterated chloroform (i.e. chloroform which has a hydrogen atom replaced by a deuterium atom) [HMDS-CDCl$_3$] Solvent

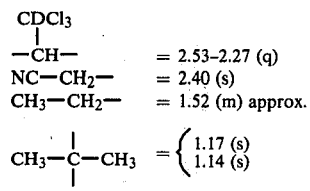

| | |
|---|---|
| CDCl$_3$ \| —CH— | = 2.53-2.27 (q) |
| NC—CH$_2$— | = 2.40 (s) |
| CH$_3$—CH$_2$— | = 1.52 (m) approx. |
| CH$_3$—C—CH$_3$ | = {1.17 (s), 1.14 (s)} |
| CH$_3$—CH$_2$— | = 1.09 (t) (J = 8 Hz) |

M.S.: m/e (relative intensity, %) 82(100), 69(45), 54(43), 68(31), 55(31), 41(30), 110(23), 39(23), 151(M+1)$^+$(13).

EXAMPLE 5

Synthesizing

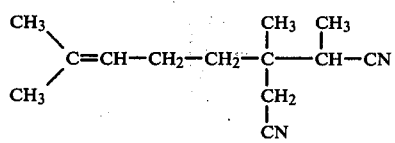

The reaction procedure (apparatus, times, temperature, order of introduction of the reactants) are the same as in EXAMPLE 1.

The following amounts are charged:

| | |
|---|---|
| ammonia | : 300 mls |
| ferric chloride | : 0.2 grams approx. |
| elemental sodium | : 5.06 grams (0.22 mol) |
| propionitrile | : 11 grams (0.2 mol) plus 20 mls of anhdrous ethyl ether |
| 3,7-dimethyl-2,6-octadienenitrile | : 29.8 grams (0.2 mol) plus 20 mls of anhydrous ethyl ether |
| ammonium chloride | : 16.8 grams (0.3 mol) slurried in 150 mls of ethyl ether. |

The raw reaction product is processed as in EXAMPLE 1.

There are obtained 31 grams (yield 76%) of 2,3,7-trimethyl-3-cyanomethyl-6-octenenitrile having a boiling point of 106° C.-108° C. under a pressure of about 0.05 mmHg.

Its principal spectroscopical characteristics are:
I.R.: stretching of —CN at about 2245 cm$^{-1}$
N.M.R.: chemical shifts relative to HMDS—Solvent CDCl$_3$

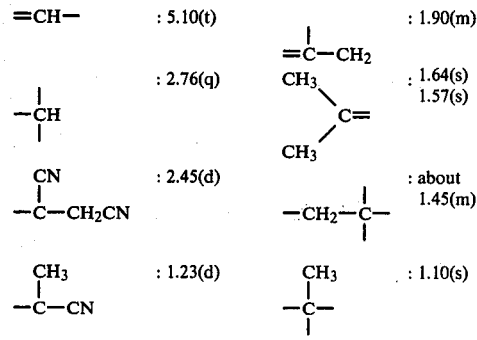

M.S.: m/e (relative intensity, %) 69(100), 41(55), 108(34), 55(27), 94(22), 150(15), 39(12), 189(11), 204(M+) (10).

EXAMPLE 6

Synthesizing 2,3,3-trimethyl pentamethylenediamine

A one-liter autoclave is charged with 40 grams of cobalt Raney (freshly prepared) and subsequently with 80 mls absolute ethanol.

After scavenging with nitrogen and then with hydrogen, commercial hydrogen is introduced under a pressure of 170 atm and then the autoclave is heated to about 105° C. for six hours. Thereafter the autoclave is cooled, the pressure is released and the autoclave is charged with a solution of 68 grams of 2,3,3-trimethyl-glutaronitrile dissolved in 30 mls abs.ethanol, the scavenging with nitrogen is repeated, there are charged 160 grams of anhydrous ammonia and finally commercial hydrogen is introduced under a pressure of 165 atm approx. The autoclave, which is fitted with a magnetic stirrer, is heated to about 105° C.-108° C. the hydrogen pressure being restored as hydrogen is gradually being absorbed. After about 2 hrs. the pressure does not decrease any more and the above specified temperature is maintained for three additional hours, whereafter the autoclave is allowed to cool. The catalyst is filtered off, the solvent is distilled off and, on the raw production of the reaction, the yield in terms of 2,3,3-trimethyl pentamethylene diamine is determined by gaschromatographic methods in the presence of an internal standard (yield 65%-70%). The diamine is then purified by fractionation and, under a pressure of about 12 Torr. it boils at 105° C.-106° C.

The principal by-product is a cyclic amine. The 2,3,3-pentamethylene diamine has been characterized by elemental analysis $^1$H.N.M.R. and $^{13}$C.N.M.R. inasmuch as the mass spectrography and the infrared analysis did not prove particularly significant.

ELEMENTAL ANALYSIS: Nitrogen: Calcd. 19.4% found 19.4%.

N.M.R. (Chemical shifts relative to HMDS—solvent CDCl$_3$)

$$H_2N-\underset{(5)}{C}-\underset{(4)}{C}-\underset{(3)(2)}{\overset{C^{(6)}}{C}}-\underset{(1)}{C}-\underset{}{C}-NH_2$$
$$\underset{C_{(8)} C_{(7)}}{}$$

$^1$H. N. M. R.

(1) $\underset{}{\overset{(5)H}{\underset{H}{\overset{|}{\underset{|}{N}}}-\overset{|}{\underset{|}{C}}-\overset{|}{\underset{|}{C}}-}}$  : ABX 2.8 ÷ 2.2 p.p.m.-8 lines (2) $-\overset{(1)}{C}H_2-NH_2$  : 2.61 p.p.m. Triplet (3) 2-NH$_2$  : 0.95 p.p.m. Singlet (4) $-\overset{(2)}{C}H_2-$  : 1.4 ÷ 1.0 p.p.m. Triplet (5) $\underset{H}{\overset{|(4)}{\underset{|}{-C-}}}$  : 1.4 ÷ 1.0 p.p.m. Multiplet (6) $-\underset{(8)}{C}H_3$  : 0.82 p.p.m. Doublet (7) $\underset{CH_3}{\overset{CH_3}{\underset{|}{-C-}}}\overset{|(3)}{}$  : 0.80 p.p.m. Singlet $^{13}$C. N. M. R.

| Carbon atoms: | 1 | 2 | 3 | 4 | 5 | 6 & 7 | 8 |
|---|---|---|---|---|---|---|---|
| Chemical shifts: | 36.9 | 44.6 | 25.4 | 45.5 | 46.1 | 23.9 | 12.2 |

EXAMPLE 7

Synthesizing 2-ethyl-3,3-dimethyl pentamethylenediamine

By adopting the same procedure as described in EXAMPLE 1, the 2-ethyl-3,3-dimethyl pentamethylenediamine has been synthesized starting from the corresponding dinitrile.

It has been characterized by $^1$H.N.M.R. and $^{13}$C.N.M.R.

N.M.R. (Chemical shifts relative to HMDS—solvent CDCl$_3$).

$$\underset{\underset{\underset{C_{(9)}}{|}}{\overset{H_2-N}{\underset{|}{C^{(7)}}} \overset{}{\underset{}{C^{(8)}}}}}{C-C-C-C-C-C-NH_2}$$
$$(6)\,(5)\,(4)\,(3)\,(2)\,(1)$$

$^1$H. N. M. R.

(1) 2-CH$_2$—NH$_2$  : 2.59 ÷ 2.89 p.p.m. multiplet (2) $-CH_2-\overset{|}{\underset{|}{CH}}-\overset{|}{\underset{|}{C}}-CH_2-$  : 1.33 ÷ 1.44 p.p.m. multiplet (3) 2-NH$_2$  : 0.98 ÷ p.p.m. singlet (4) CH$_3$—  : 0.94 p.p.m. triplet (5) $\underset{CH_3}{\overset{CH_3}{\underset{|}{-C-}}}$  : 0.82 ÷ 0.84 p.p.m. singlet $^{13}$C. N. M. R.

| | | |
|---|---|---|
| C$_1$: | 37.6 p.p.m. | triplet |
| C$_2$: | 42.5 p.p.m. | triplet |
| C$_3$: | 35.5 p.p.m. | singlet |
| C$_4$: | 52.7 p.p.m. | doublet |
| C$_5$: | 21.4 p.p.m. | triplet |
| C$_6$: | 14.4 p.p.m. | quadruplet |
| C$_7$: | 45.1 p.p.m. | triplet |
| C$_8$ & C$_9$: | 25.5 p.p.m. | quadruplet |

EXAMPLE 8

Synthesizing poly-(2,3,3-trimethyl-pentamethylene)terephthalamide

A solution containing 4.54 grams (0.0315 mol) of 2-ethyl-3,3-dimethylpentamethylenediamine, purified by fractionation, and 0.0630 mol of sodium hydroxide in 2.25 liters of water, is poured in a 5-liter beaker and stirred by a high-speed stirring device.

A solution of 6.4 grams (0.0315 mol) of terephthaloyl chloride is rapidly poured in the stirred solution. The polymerization mixture is stirred during 15 mins. at room temperature. The resultant mixture is then filtered, washed with hot water and subsequently with a cold aqueous solution of sodium bicarbonate, and eventually with cold plain water. The mixture is then placed in a Soxhlet extractor with ethanol and then dried in a vacuum oven at 70° C.

The polymer thus obtained has an inherent viscosity, $\eta$, of 0.86 (solution at 0.5% conc. in 98% sulphuric acid at 30° C.). The X-ray analysis both on the polymer as such and on the annealed polymer (215° C. for 30 mins.

annealing) did not show any appreciable traces of crystallinity.

The D.S.C. thermal analysis has permitted to identify at 175° C.-178° C. the glass transition and no appreciable phenomena of decomposition are experienced up to a temperature of 300° C.

EXAMPLE 9

Synthesizing poly-(2-ethyl-3,3-dimethyl pentamethylene)-terephthalamide

By adopting the same procedure described in EXAMPLE 8, poly-(2-ethyl-3,3-dimethyl pentamethylene)-terephthalamide has been prepared starting from 2-ethyl-3,3-dimethyl pentamethylenediamine and terephthaloyl chloride. The polymer thus obtained (inh.$\eta$=0.71 in a 0.5% soln. of 98% $H_2SO_4$ at 30° C.) does not show at the X-ray inspection any appreciable traces of crystallinity, even after annealing at 230° C. for 30 mins. The DSC thermal analysis has permitted to localize at 160° C.-162° C. the glass transition.

We claim:

1. A method of preparing a dinitrile compound represented by the formula:

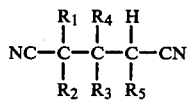

when a saturated nitrile represented by the formula:

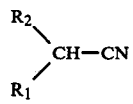

is reacted with an unsaturated nitrile represented by the formula:

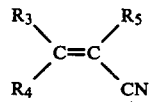

and wherein $R_1$ and $R_2$ are the same or different and are selected from the group consisting of hydrogen, an aliphatic hydrocarbon radical which may be substituted with a cycloaliphatic hydrocarbon radical and a cycloaliphatic hydrocarbon radical, $R_3$ and $R_4$ are the same or different and are selected from the group consisting of an aliphatic hydrocarbon radical which may be substituted with a cycloaliphatic hydrocarbon radical and a cycloaliphatic hydrocarbon radical, and $R_5$ is selected from the group consisting of hydrogen, an aliphatic hydrocarbon radical, cyclopropyl or phenyl, said method comprising (a) contacting said saturated nitrile with a strong base in an amount from 1 to 5 mols of strong base per mol of said saturated nitrile in the presence of a solvent selected from the group consisting of ammonia, ethylether, tetrahydrofuran, and hexane to form a reaction mixture whereby said saturated nitrile is ionized, (b) reacting said unsaturated nitrile with said ionized saturated nitrile for one to 60 minutes to form a second reaction mixture, and (c) adding an acid or a salt of a strong acid and a weak base to said second reaction mixture to thereby stop the reaction, and wherein said method is conducted at a temperature of from −80° C. to −10° C.

2. The method as claimed in claim 1 wherein said salt of a strong acid and said weak base is ammonium chloride.

3. The method as claimed in claim 1 wherein said temperature is from −50° C. to −10° C.

4. The method as claimed in claim 1 wherein said unsaturated nitrile is reacted with said ionized saturated nitrile for three to ten minutes.

5. The method as claimed in claim 1 wherein said aliphatic hydrocarbon radical has from one to ten carbon atoms and said cycloaliphatic hydrocarbon radical has from three to ten carbon atoms.

6. The method as claimed in claim 1, wherein said strong base is a member of the group consisting of the amides of alkali metals, the hydrides of alkali metals, the hydrides of alkaline earth metals and the metal alkyls.

7. The method as claimed in claim 1, wherein from 1 to 1.8 mols of strong base are used for each mol of saturated nitrile.

* * * * *